United States Patent [19]

Udaka et al.

[11] Patent Number: 4,946,789
[45] Date of Patent: Aug. 7, 1990

[54] *BACILLUS BREVIS* STRAINS AND APPLICATION THEREOF

[75] Inventors: Shigezo Udaka, Aichi; Hiroaki Takagi; Kiyoshi Kadowaki, both of Chiba, all of Japan

[73] Assignee: Higeta Shoyu Co., Ltd., Tokyo, Japan

[21] Appl. No.: 43,459

[22] Filed: Apr. 28, 1987

[30] Foreign Application Priority Data

Aug. 26, 1986 [JP] Japan .................................. 61-198120

[51] Int. Cl.$^5$ ........................ C12N 1/20; C12N 15/00; C12P 21/00
[52] U.S. Cl. ............................ 435/252.3; 435/252.31; 435/69.1; 435/71.1; 435/71.2; 435/172.3; 435/172.1; 935/29; 935/38; 935/61; 935/74
[58] Field of Search .............. 435/243, 68, 253, 172.3, 435/172.1, 833

[56] References Cited

U.S. PATENT DOCUMENTS

| | | | |
|---|---|---|---|
| 4,590,159 | 5/1986 | Markovitz et al. | 435/68 |
| 4,758,512 | 7/1988 | Goldberg et al. | 435/68 |
| 4,828,994 | 5/1989 | Fahnestock | 435/172.3 |

FOREIGN PATENT DOCUMENTS 0060663 of 1982 European Pat. Off. .
8601825 of 1986 PCT Int'l Appl. .

OTHER PUBLICATIONS

Nakamura et al., BBRC 128: 601–606 (1985).
Downs et al., J. Bacter. 165: 193–197 (1986).
Udaka et al., Eur. Congr. Biotechnol. 3rd, vol. 3, 415-19 Verlag Chemie Weinheim Fed. Rep. Ger.
Biotechnology Newswatch (McGraw-Hill's) vol. 4, issue 20, p. 6.
Chemical Abstracts, vol. 101, Abstract 123914.
Chemical Abstracts, vol. 100, No. 5, Jan. 1984, p. 105, Abstract No. 30363w, Columbus, Ohio, U.S.
Agricultural and Biological Chemistry, vol. 46, No. 1, Jan. 1982, pp. 65–74.
Chemical Abstracts, vol. 106, 1987, p. 382, Abstract No. 172516w, Columbus, Ohio, U.S.

*Primary Examiner*—Richard A. Schwartz
*Assistant Examiner*—Anne Brown
*Attorney, Agent, or Firm*—Browdy and Neimark

[57] ABSTRACT

*Bacillus brevis* strains which produce a large amount of protein but no protease out of the cells are disclosed. These strains are highly useful as hosts in genetic engineering.

2 Claims, 2 Drawing Sheets

BACILLUS BREVIS STRAINS AND APPLICATION THEREOF

FIELD OF THE INVENTION

This invention relates to novel *Bacillus brevis* strains. More particularly, it relates to novel *Bacillus brevis* strains which are useful as hosts in genetic engineering.

BACKGROUND OF THE INVENTION

*Escherichia coli* has been generally used as a host in genetic engineering. However, the use of *E. coli* has many disadvantages such as that peptides or proteins produced by recombined genes would not be secreted into media but remain within the cells, so that their production will be naturally limited, and therefore that the extraction and purification of the peptides or proteins involve complicated procedures such as cell grinding and affinity chromatography.

Udaka et al. studied to find microorganisms capable of secreting proteins out of the cells as hosts for genetic engineering, and consequently isolated and identified five strains including four belonging to *B. brevis* and one belonging to *Bacillus proteiformans* each secreting a large amount of proteins, among approximately 1,200 strains (cf. Agric. Biol. Chem., 40 (3), 523–528 (1976)).

Also *B. subtilis* is used as a secreting host and used to obtain accumulation of various heterologous proteins including α-amylase and interferon. However these attempts do not necessarily give satisfactory results, since proteases present inside or outside the cells would restrict the amount of the products or even decompose the same.

Previously Udaka et al. found that *B. brevis* 47, which harbored pBAM101 obtained by introducing a thermostable α-amylase gene of *Bacillus stearothermophilus* DY-5 into plasmid pUB110, and *B. subtilis* harboring pBAM101 produced approximately 15,000 U/ml and 3,000 U/ml of α-amylase in media respectively when cultured at 37° C. for 48 hours (cf. J. Bacteriol., 164 (3), 1182–1187 (1985)).

Thus it has been proved that a heterologous gene product can be efficiently produced by utilizing the protein-secreting ability of a protein-producing bacterium, *B. brevis* 47, since *B. brevis* 47, which will be described in detail hereinbelow, can produce a thermostable α-amylase approximately five times as much as *B. subtilis*, having the same plasmid as that in the former, does.

However, all of the above-mentioned five strains, each isolated as a bacterium capable of secreting a large amount of protein out of the cells, i.e., *B. brevis* 47, 144, 481 and 899 and *B. proteiformans* 444, would decompose bovine serum albumin, which will be abbreviated as BSA hereinafter, when grown in a medium containing BSA. In addition, it has been proved that *B. brevis* 144, 481 and 899 and *B. proteiformans* 444 are further capable of decomposing casein. These facts suggest that peptides and proteins efficiently produced by these bacteria, each employed as a host capable of secreting a large amount of protein out of the cells in the production of a heterologous gene product with the use of a recombined gene, may be decomposed with protease.

SUMMARY OF THE INVENTION

From the viewpoint that a microbial strain capable of secreting a large amount of protein but no protease out of the cells can be used as an excellent host in genetic engineering, we have searched such a strain as described above among approximately 100,000 strains isolated from various samples and consequently succeeded in isolating two strains which produce a large amount of protein but no protease out of the cells. Both of these two strains thus isolated have been identified to belong to *B. brevis*. Thus the present invention has been completed.

The present invention provides *B. brevis* strains which produce a large amount of protein but no protease out of the cells.

The present invention further provides hosts in genetic engineering which are *B. brevis* strains capable of producing a large amount of protein but no protease out of the cells.

There have been known some *B. brevis* strains which produce protein. However every known strain produces protease out of the cells. Thus the *B. brevis* strains of the present invention, which produce a large amount of protein but no protease out of the cells, are completely novel ones.

DETAILED DESCRIPTION OF THE INVENTION

Figure 1A:
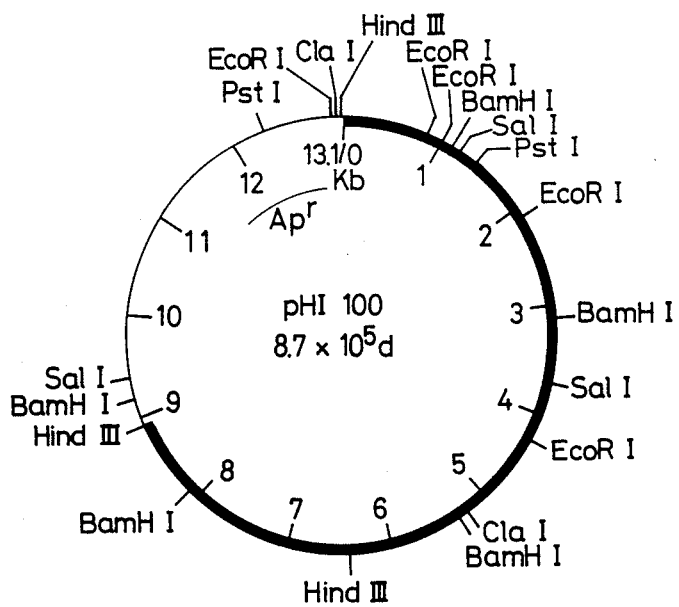
FIGS. 1-*a*, *b* and *c* show the restriction enzyme maps of pHI100, pHI301 and pHI300, respectively, wherein a thick line represents a DNA originating from *B. stearothermophilus* while a fine line represents pBR 322 DNA. Ap shows the locus of a β-lactamase gene.

In the present invention, the selection of strains is effected in order to isolate those which secrete 5 g/l or more of protein in media and decompose neither BSA nor casein.

First, approximately 100,000 strains isolated from various samples such as soils were inoculated to T2 agar plate medium (pH 7.0) comprising 1% of glucose, 1% of peptone, 0.5% of meat extract, 0.2% of yeast extract and 1.5% of agar powder. Then 5% perchloric acid was added to the culture and strains showing turbidity around colonies were selected. The isolated strains were cultured in 10-ml portions of T2 liquid medium in a 150-ml Erlenmeyer flask under shaking at 30° C. for 48 hours. Thus 80 strains, each producing 1.2 g/l or more of protein in the culture filtrate, were obtained.

The extracellular protein was determined by adding the same amount of 0.2 N NaOH to the medium; stirring and centrifuging the resulting mixture at 10,000 rpm for five minutes to thereby remove the cells; adding the same amount of 10% trichloroacetic acid to the supernatant; centrifuging the resulting mixture after ten minutes at 3,000 rpm for ten minutes to thereby collect the precipitate; dissolving the obtained precipitate in 1 N NaOH; and determining the protein by Lowry's method (cf. J. Biol. Chem., 193, 265 (1951)). The amount of the protein was expressed in terms of BSA.

Table 1 shows media selected for efficient production of protein.

TABLE 1

| Composition/Medium | Media for efficient production of protein | | | | |
|---|---|---|---|---|---|
|  | 5 YKC | 5 Y | 5 KC | 1 Y | 1 K |
| Glucose | 5.0% | 5.0% | 5.0% | 1.0% | 1.0% |
| Polypeptone | 3.0 | 3.0 | 3.0 | 3.0 | 3.0 |
| Yeast extract | 0.2 | 0.2 |  | 0.2 |  |

TABLE 1-continued

| Composition/Medium | Media for efficient production of protein | | | | |
|---|---|---|---|---|---|
| | 5 YKC | 5 Y | 5 KC | 1 Y | 1 K |
| $K_2HPO_4$ | 0.1 | | 0.1 | | 0.1 |
| $CaCl_2$ | 0.01 | | 0.01 | | |
| $MgSO_4\ 7H_2O$ | 0.01 | 0.01 | 0.01 | 0.01 | 0.005 |
| $FeSO_4\ 7H_2O$ | 0.001 | 0.001 | 0.001 | 0.001 | 0.0005 |
| $MnSO_4\ 4H_2O$ | 0.001 | 0.001 | 0.001 | 0.001 | 0.0005 |
| $ZnSO_4\ 7H_2O$ | 0.0001 | 0.0001 | 0.0001 | 0.0001 | 0.00005 |
| pH | 7.2 | 7.2 | 7.2 | 7.2 | 7.2 |

80 strains as mentioned above, respectively, were inoculated to each of these five media, and then cultured under shaking. Thus 31 strains producing 5 g/l or more of extracellular protein in one or more of these media were selected.

These 31 strains' capabilities of decomposing BSA and milk casein were determined in the following manner.

DETERMINATION OF THE CAPABILITY OF DECOMPOSING BSA 10-ml portions of T2 medium were pipetted into 150-ml Erlenmeyer flasks and sterilized in an autoclave. Then an aseptically filtered BSA solution (Sigma A4503) was added to the medium in each flask to give a final concentration of 3.2 mg/ml. The medium was inoculated with 0.2 ml of a strain cultured overnight. Then the strain was cultured therein under shaking at 200 rpm at 37° C.

Filtrate samples collected 24 hours, 48 hours and 72 hours after the initiation of the culture were centrifuged at 10,000 rpm for five minutes. To 625 μl of each supernatant thus obtained, 125 μl of 0.5M Tris-HCl (pH 6.8), 200 μl of 10% SDS and 50 μl of β-mercaptoethanol were added and the mixture was stirred. After thermally treating the mixture in boiling water for three minutes, 0.1 ml of 0.0625M Tris-HCl (pH 6.8) containing 0.05% of BPB and 70% of glycerol was added thereto to give a sample for sodium dodecyl sulfatepolyacrylamide gel electrophoresis (SDS-PAGE). Slab SDS-PAGE was carried out at an acrylamide concentration of 10%. Protein was detected by Coomassie Brilliant Blue staining. Thus strains which did not decompose BSA in any of 24, 48 and 72 hours culture, were regarded as having no capability of decomposing BSA.

DETERMINATION OF THE CAPABILITY OF DECOMPOSING MILK CASEIN 5 g, 2 g and 1 g of skim milk were suspended each in 50 ml of distilled water. Separately 1-g portions of agar were dissolved each in 50 ml of distilled water. After separately sterilizing in an autoclave, the suspensions were mixed with the solutions and pipetted into Petri dishes to give 5%, 2% and 1% milk agar media. Each strain was inoculated to these plate cultured therein at 37° C. for three days to observe whether the periphery of each colony would become clear or not. Thus strains showing no clear halo around their colonies in any of the 5%, 2% and 1% milk agar media were regarded as having no capability of decomposing milk casein.

Consequently, H102 and H503 strains, which proved to decompose neither BSA nor milk casein in the above-mentioned tests, were selected as those producing no protease out of the cells. Table 2 shows examples of the production of protein by the H102 and H503 strains in the media as shown in Table 1.

TABLE 2

| Extracellular protein productivites of H102 and H503 strains | | | | | |
|---|---|---|---|---|---|
| | Produced protein (g/l) | | | | |
| | 5 YKC | 5 Y | 5 KC | 1 Y | 1 K |
| H102 | 8.1 | 4.1 | 5.3 | 5.7 | 6.9 |
| H503 | 7.6 | 2.3 | 1.6 | 0.9 | 0.6 |

The H102 and H503 strains were identified according to methods described in Bergey's Manual of Determinative Bacteriology (8th ed.) and the prokaryote (A Handbook on Habitats, Isolation and Identification of Bacteria). As a result, both strains are considered to belong to the genus Bacillus since they are aerobic, gram-positive and bacilli and show sporulation. Further both strains are identified to belong to *B. brevis* since they are positive to catalase and negative in V-P reaction; can not grow at 65° C.; do not decompose any starches; can not grow under anaerobic conditions; form acid from glucose in a medium comprising 7 g/l of proteose peptone, 5 g/l of NaCl, 5 g/l of glucose and 0.008 g/l of bromocresol purple; and can not grow in the presence of 7% of NaCl. Although it is believed that *B. brevis* decomposes casein, these two strains show no capability of decomposing the same.

Accordingly the two strains are named *B. brevis* H102 and *B. brevis* H503. They have been deposited as FERM BP-1087 and FERM BP-1088, respectively, with Fermentation Research Institute, Agency of Industrial Science and Technology, Japan.

Now the microbiological properties of *B. brevis* H102 and H503 will be shown.

| (A) Morphological properties | | |
|---|---|---|
| | *B. brevis* H102 | *B. brevis* H503 |
| Cell size (μ) | 0.4–0.6 × 1.5–4 | 0.4–0.6 × 1–2 |
| Cell form | bacillus | bacillus |
| Polymorphism | no | no |
| Motility | yes (peritrichal) | yes (peritrichal) |
| Sporulation | yes | yes |
| Spore form | oval | oval |
| Sporulation portion | center - ends | center - ends |
| Spore size (μ) | 0.5 × 1.5–2 | 0.5 × 1–2 |
| Sporangium form | swollen | swollen |
| Gram-stain | + | + |
| Acid-fastness | no | no |
| (B) Growth in various media | | |
| | H102 | H503 |
| Bouillon agar plate medium (30° C., 2 days) | | |
| Growth | somewhat poor | good |
| Surface | smooth | smooth |
| Color | pale yellowish brown | pale yellowish brown |
| Gloss | glossy, translucent | somewhat glossy, turbid |
| Form | circular | circular |
| Rising | flat - convex | flat - convex |
| Edge | full | full |
| Bouillon agar slant medium | | |
| Growth | medium | medium |
| Surface | smooth - somewhat coarse | smooth |
| Color | light brownish gray | light brownish gray |
| Gloss | glossy | glossy |
| Form | filaria | filaria |
| Bouillon liquid medium | | |
| Turbidity | no | significant |
| Growth on | scattered | filmy |

-continued

| | H102 | H503 |
|---|---|---|
| liquid surface Precipitate | trace | medium |
| Gelatin stab culture | | |
| Growth | surface | surface |
| Liquefaction | none | none |
| Litmus milk | | |
| Reduction | no | alkaline |
| Agglutination and Lique-faction | not liquefied | not liquefied |
| (C) Physiological properties | | |
| | H102 | H503 |
| Reduction of nitrate | − | − |
| Denitrification | − | − |
| MR test | − | + |
| VP test acetoin formation | − | − |
| Indole formation | − | − |
| Hydrogen sulfide formation | + | + |
| Hydrolysis of starch | − | − |
| Utilization of citric acid | | |
| Koser | + | + |
| Christensen | + | + |
| Utilization of inorganic nitrogen source | | |
| nitrate | − | + |
| ammonium salt | + | + |
| Dye formation (King's medium) | − | fluorescent yellowish green |
| Urease | − | + |
| Oxidase | + | + |
| Catalase | + | + |
| Growth pH (optimum pH) | 6–8.5 (7–8) | 5–9 (6–8.5) |
| Maximum growth temp. | 40° C. | 45° C. |
| Optimum temp. | 30–40° C. | 30–40° C. |
| Attitude to oxygen | aerobic | aerobic |
| O-F test (Hugh-Leifson method) | not decomposed | oxidized (O) |
| Decomposition of casein | − | − |
| Decomposition of DNA | − | − |
| Resistance to NaCl: 2% | − | + |
| 5% | − | + |
| 7% | − | − |
| Acid formation from glucose | + | + |

| Formation of acid and gas from carbon source (−: none) | | | | |
|---|---|---|---|---|
| | H102 | | H503 | |
| | Acid | Gas | Acid | Gas |
| L-arabinose | − | − | − | − |
| D-xylose | − | − | − | − |
| D-glucose | − | − | − | − |
| D-mannose | − | − | − | − |
| D-fructose | − | − | − | − |
| D-galactose | − | − | − | − |
| Maltose | − | − | − | − |
| Sucrose | − | − | − | − |
| Lactose | − | − | − | − |
| Trehalose | − | − | − | − |
| D-sorbitol | − | − | − | − |
| D-mannitol | − | − | − | − |
| Inositol | − | − | − | − |
| Glycerol | − | − | − | − |
| Starch | − | − | − | − |

Typical examples of the B. brevis strains of the present invention, which produces a large amount of protein but no protease out of the cells, include B. brevis H102 and H503.

The proteins per se produced in a large amount by the novel B. brevis strains of the present invention are highly useful in the art, for example, as food materials such as edible proteins, a gelling agent or an inflating agent or as industrial materials such as surface treating agents for vitreous material, paper or artificial leather.

The novel B. brevis strains of the present invention can efficiently secrete products obtained by genetic engineering out of the cells and do not decompose said products. Thus they are excellent hosts in genetic engineering.

It is very useful in the art to apply the above-mentioned mechanism to various fields as, for example, pharmaceuticals, food materials including excellent edible proteins, a gelling agent and an inflating agent or industrial materials including surface treating agents for vitreous material, paper or artificial leather.

As described above, the present invention is highly useful in the art.

Now an application example of the novel B. brevis strain of the present invention will be given.

APPLICATION EXAMPLE

Cloning of Thermophilic α-amylase Gene into E. Coli

The chromosomal DNA of thermophilic Bacillus stearothermophilus DY-5 was partially digested with a restriction enzyme HindIII. Separately, pBR322, which is a plasmid vector of E. coli, was completely digested with HindIII and then treated with alkaline phosphatase. These DNAs were mixed together and bound to each other with T4 DNA ligase. Thus the E. coli was transformed and α-amylase-producing strains were selected from the transformed strains which were resistant against ampicillin and sensitive to tetracycline. The transformed strains were placed on a filter paper with the colony side up and bacteriolyzed from the downside. Then the filter paper was placed on a plate containing 1% of soluble starch with the colony side down and maintained at 37° C. overnight. Then strains showing a clear zone around each colony were selected by the iodostarch reaction. In the case of a transformed strain showing a significantly high activity, halo can be observed by replicating said transformed strain to a medium containing 1% of soluble starch and directly effecting the iodo-starch reaction.

Figure 1B:
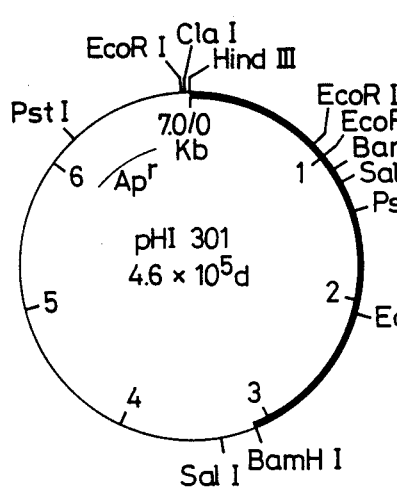
Figure 1C:
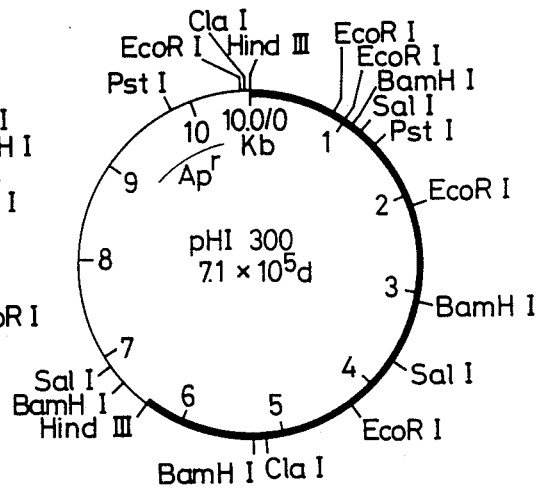

Thus four α-amylase-producing strains (HI100 to HI400) were isolated from approximately 6,000 transformed strains. The results of the analysis of the plasmids carried by these strains suggest that pHI100 has HindIII fragments of 6.4 Kb and 2.5 Kb originating from the B stearothermophilus DNA while pHI200 to pHI400 have the same HindIII DNA fragment of 6.4 Kb. FIG. 1 shows the restriction enzyme maps thereof. Since pHI300 still carried the longer DNA fragment of 6.4 Kb, the plasmid was reduced to give pHI301 carrying a DNA fragment of 3.2 Kb.

SUBCOLONING OF THERMOPHILIC α-AMYLASE GENE

Figure 2:
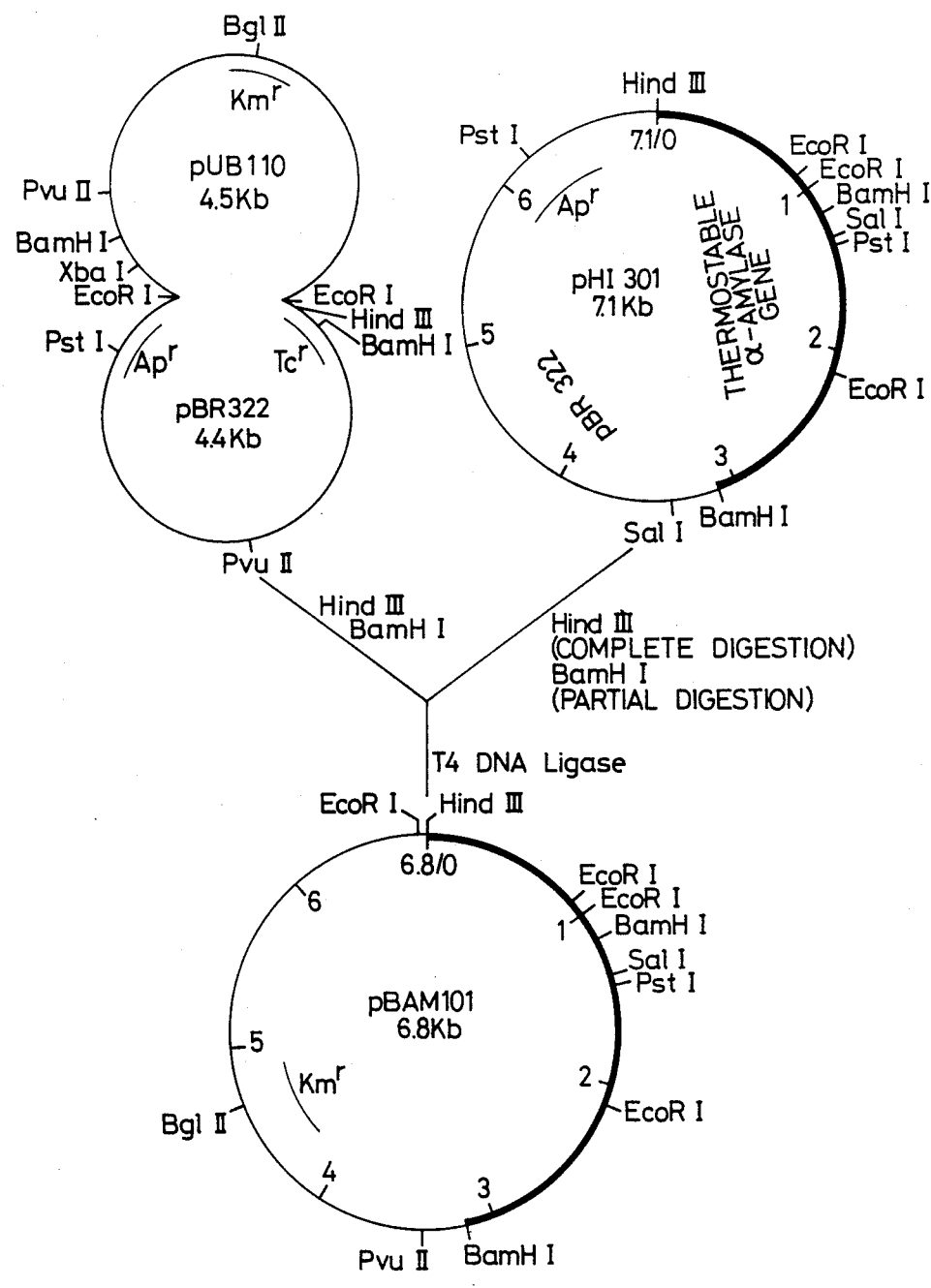
FIG. 2 shows subcloning of an α-amylase gene on pUB110.

In order to express an α-amylase gene in gram-positive bacteria, such as B. subtilis or protein-producing bacteria, it is required to transfer the α-amylase gene to a plasmid replicatable in gram-positive bacteria, for example, plasmid pUB110. Thus subcloning was effected by the process as shown in FIG. 2. Since no HindIII breakage point existed on the pUB110, a complex plasmid of pUB110 and pBR322 was first prepared. The obtained complex plasmid was completely digested with HindIII and BamHI and then treated with alkaline phosphatase. Separately, pHI301 containing the α-amylase gene was completely digested with HindIII and then partially digested with BamHI. These DNAs were mixed together and ligated to each other with T4 DNA ligase. B. subtilis 1A289, which produced no α-amylase, was transformed by the protoplast method and an α- amylase-producing strain resistant to kanamycin was selected. The α-amylase-producing strain of *B. subtilis* had a plasmid pBAM101 involving the complete α-amylase gene on the pHI301, as planned initially.

Then *B. brevis* H102 producing no α-amylase, which is one of the strains of the present invention, and *B. brevis* 47 and 899, which had a protease and produced no α-amylase, were transformed with the use of the pBAM101 by the Tris-PEG method (cf. J. Bacteriol., 156, 1130–1134 (1983)). Subsequently α-amylase-producing strains resistant to neomycin were selected and transformed strains carrying pBAM101 were isolated.

PROPERTIES OF α-AMYLASE PRODUCED BY VARIOUS HOSTS

The properties of α-amylases produced by *B. subtilis* 1A289 and by protein-producing *B. brevis* H102, 47 and 899, the four strains harboring pBAM101, were compared with those of α-amylase produced by thermophilic *B. stearothermophilus* DY-5. Consequently, the former α-amylases were completely the same as the latter in the thermostability and thermophilicity. Namely, the former α-amylases were stable up to approximately 80° C. and showed the optimum temperature range of 70° to 80° C. And their molecular weights were almost the same, i.e., approximately 60,000.

AMYLASE PRODUCTIVITIES IN VARIOUS HOSTS

*B. subtilis* 1A289 and protein-producing *B. brevis* H102, 47 and 899, the four strains harboring pBAM101, were cultured at 37° C. under shaking. Each culture liquor was sampled at given intervals and centrifuged at 10,000 rpm for five minutes. Then the α-amylase activity in the obtained supernatant was determined according to Fuwa's method at 40° C.

Thus the *B. subtilis*, protein-producing *B. brevis* H102 having no capability of decomposing protein, and *B. brevis* 47 and 899 each capable of decomposing protein accumulated 50 U/ml, approximately 30,000 U/ml, approximately 1,300 U/ml and 1,600 U/ml of α-amylase in the media, respectively, when cultured in 5Y medium with 60 μg/ml of neomycin for 48 hours.

What is claimed is:

1. A *Bacillus brevis* selected from the group consisting of *Bacillus brevis* H102 (FERM BP-1087) and *Bacillus brevis* H503 (FERM BP-1088) strain in substantially pure form.

2. A method of preparing a desired exopeptide or exoprotein by means of recombinant DNA, which comprises using as a host a *Bacillus brevis* selected from the group consisting of *Bacillus brevis* H102 (FERM BP-1087) and *Bacillus brevis* #503 (FERM BP-1088) capable of producing exoprotein but incapable of producing exoprotease which decomposes bovine serum albumin and also incapable of producing exoprotease which decomposes casein.

* * * * *